US00PP34792P2

(12) United States Plant Patent
Chaparro

(10) Patent No.: US PP34,792 P2
(45) Date of Patent: Dec. 6, 2022

(54) PEACH TREE NAMED 'UFRUBY'

(50) Latin Name: *Prunus persica*
Varietal Denomination: UFRuby

(71) Applicant: Florida Foundation Seed Producers, Inc., Marianna, FL (US)

(72) Inventor: Jose X. Chaparro, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 21 days.

(21) Appl. No.: 17/803,264

(22) Filed: Apr. 8, 2022

(51) Int. Cl.
*A01H 6/74* (2018.01)
*A01H 5/08* (2018.01)

(52) U.S. Cl.
USPC ..... Plt./197

(58) Field of Classification Search
USPC ..... Plt./197
See application file for complete search history.

(56) References Cited

U.S. PATENT DOCUMENTS

PP14,764 P2 5/2004 Sherman
PP20,294 P2 9/2009 Chaparro

*Primary Examiner* — Annette H Para
(74) *Attorney, Agent, or Firm* — Katherine Koenig; Koenig IP Works, PLLC

(57) ABSTRACT

A new and distinct cultivar of peach tree plant named 'UFRuby'. This new cultivar has a moderate winter chilling requirement estimated at 200 chill units (cu). The tree is medium size, moderately vigorous, and semi-spreading in growth habit. It bears showy, pink flowers, and leaves have reniform glands. Trees of 'UFRuby' are self-fertile and regularly bear heavy annual crops of early season fruit that are of medium size (approximately 118 g) for its ripening season. Fruit are clingstone, uniformly firm with non-melting white and smooth-textured flesh. Fruit are nearly round, and uniform with a substantially symmetrical shape, have an attractive 60%-70% red skin, ripen evenly, and are of high eating quality. The fruit of 'UFRuby' usually ripen in late April in Gainesville, Fla.

3 Drawing Sheets

Genus and species: *Prunus persica.*
Cultivar denomination: 'UFRuby'.

CROSS-REFERENCE TO RELATED APPLICATIONS

N/A.

ACKNOWLEDGEMENT OF FEDERAL RESEARCH SUPPORT
N/A.

BACKGROUND OF THE NEW CULTIVAR

The present invention relates to a new and distinct cultivar of peach (*Prunus persica* (L.) Batsch) tree adapted to a subtropical (moderate chill) winter climate. This new tree, hereinafter referred to by the name 'UFRuby', produces fruit that are highly colored, of good eating quality, and that have white and non-melting flesh, for fresh market in late April in Gainesville, Fla. The new peach cultivar 'UFRuby' is a promising candidate for commercial success in that it has attractive red skin and sweet fruit that ripen evenly.

'UFRuby' peach tree (genotype) originated in a cultivated area of the fruit breeding program at the University of Florida, located in Gainesville, Fla., where it was tested. 'UFRuby' was selected in 2009 because it exhibited white, non-melting flesh, in a medium size fruit with a bright red skin. 'UFRuby' was asexually propagated by budding onto 'Flordaguard' (unpatented) seedling rootstock (for root-knot nematode control) and determined to have unique tree and fruit characteristics making it worthy for commercial fresh fruit production. There are no known effects of this standard rootstock on this scion cultivar. Asexually propagated plants remained true to the original tree and all characteristics of the tree and the fruit have transmitted for two generations.

Plant Breeder's Rights for this cultivar have not been applied for. The new peach cultivar 'UFRuby' has not been made publicly available more than one year prior to the filing of this application.

SUMMARY OF THE INVENTION

'UFRuby' peach tree is a new and distinct variety that bears fruit having white, non-melting flesh, and having good flavor, brix, and eating quality. The flowers of 'UFRuby' bloom in late January and fruit of 'UFRuby' ripen in late April in Gainesville, Fla. Thus, the chilling requirement is estimated at 200 chill units. The trees are vigorous, productive, and without alternate bearing. Trees attain in two years a height of two meters and a spread of one and half meters in Gainesville. Terminal growth of up to a half meter annually is common on mature five-year-old trees with normal pruning to a vase shape.

The first fruit of 'UFRuby' ripen the week following mid-April in Gainesville, Fla., or in about 68 days from full bloom. The fruit are uniformly medium in size, averaging 118 g when properly thinned to a full crop, and have non-melting white flesh. Ripe fruit have, on average, 60%-70% red blush, with some red pigment in the flesh but not at the pit. The tree bears showy pink flowers with deep yellow anthers, and leaf glands are reniform. No buttons (parthenocarpy fruit) or split pits have been observed.

Plant of the new peach cultivar 'UFRuby' can be compared to plants of 'UFSun' (U.S. Plant Pat. No. 14,764), a standard peach variety. In side-by-side comparisons conducted in Gainesville, Fla., plants of the new peach cultivar 'UFRuby' differed from plants of 'UFSun' in the following characteristics:

1. fruit of 'UFRuby' are more rounded than fruit of 'UFSun', which are longer;
2. flowers of 'UFRuby' bloom about three to eight days after those of 'UFSun'; and
3. first fruit of 'UFRuby' typically ripen later than those of 'UFSun' (0-2 days after 'UFSun' in most years).

DESCRIPTION OF THE FIGURES

The accompanying photographs (as shown in FIGS. 1-3) illustrate the overall appearance of the new peach cultivar 'UFRuby' These photographs show the colors as true as can be reasonably obtained in colored reproductions of this type. Colors in the photographs may differ slightly from the color values cited in the detailed botanical description, which accurately describe the colors of the new peach cultivar.

DETAILED BOTANICAL DESCRIPTION OF THE CULTIVAR

Figure 1:
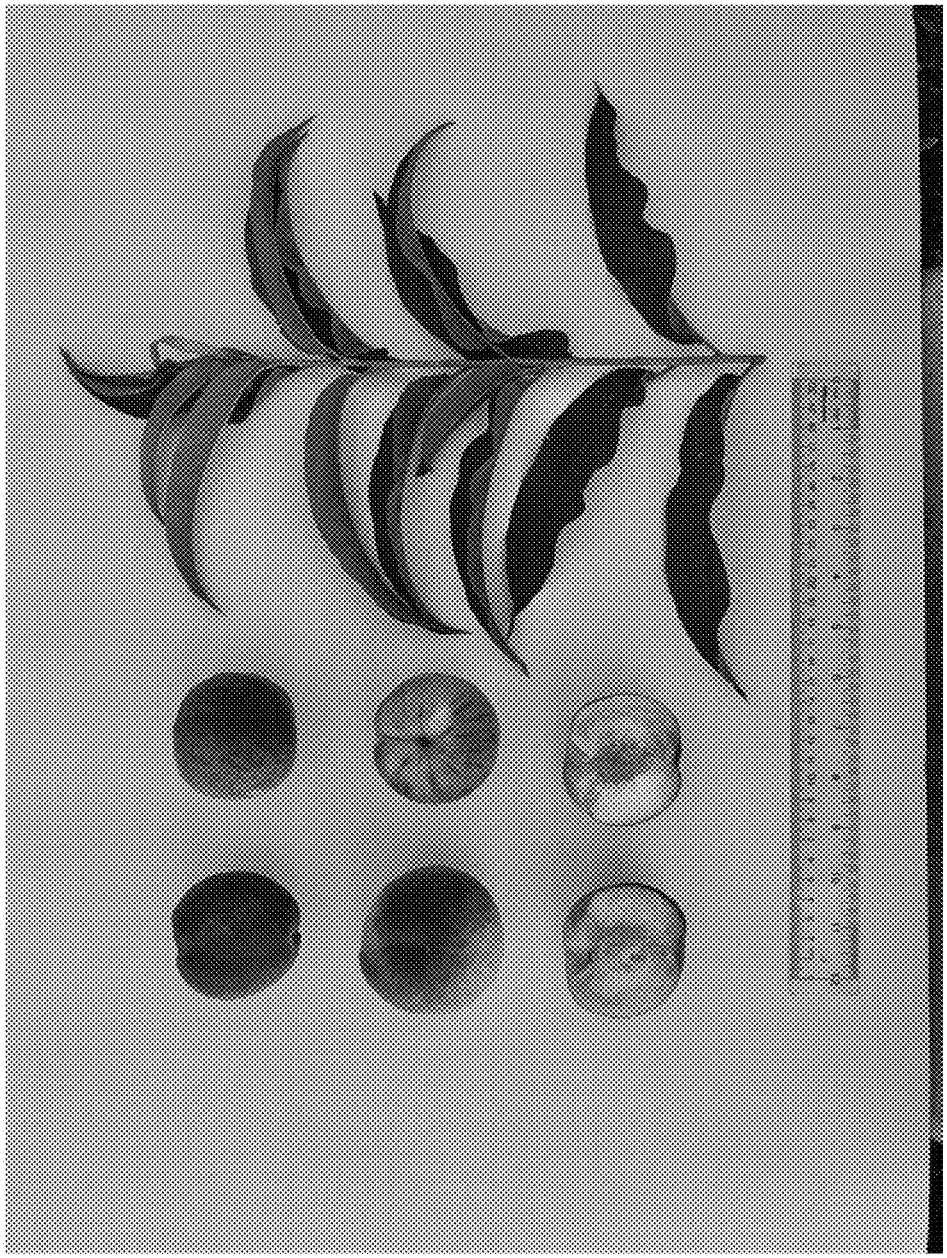
FIG. 1 shows a various views of the fruit (side view, stem end view, blossom end view, side views showing the structure of a fruit cut longitudinally to show the fruit with and without the pit) and mature leaves of the new peach cultivar 'UFRuby'.
Figure 2:
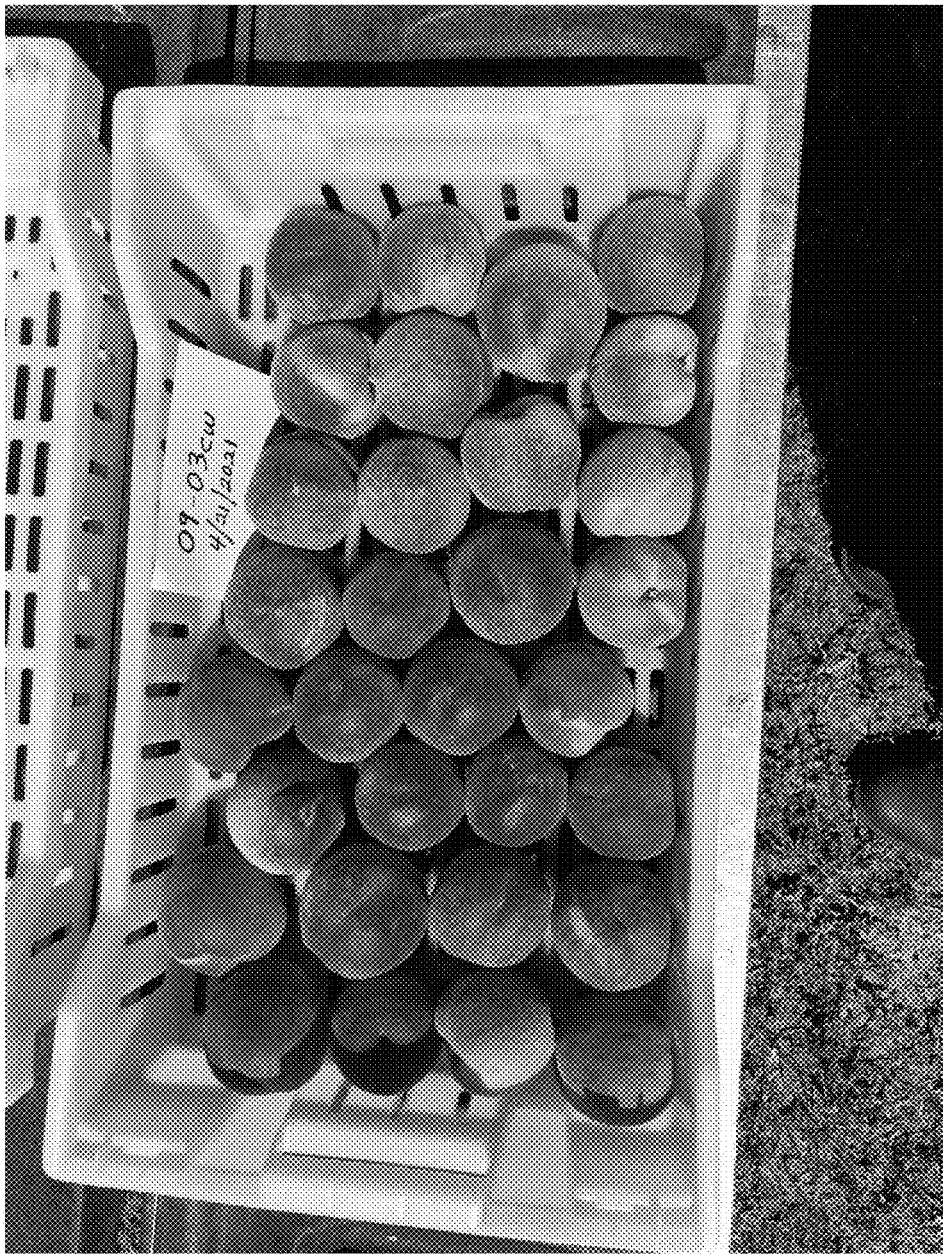
FIG. 2 shows an additional view of the fruit of the new peach cultivar 'UFRuby'.
Figure 3:
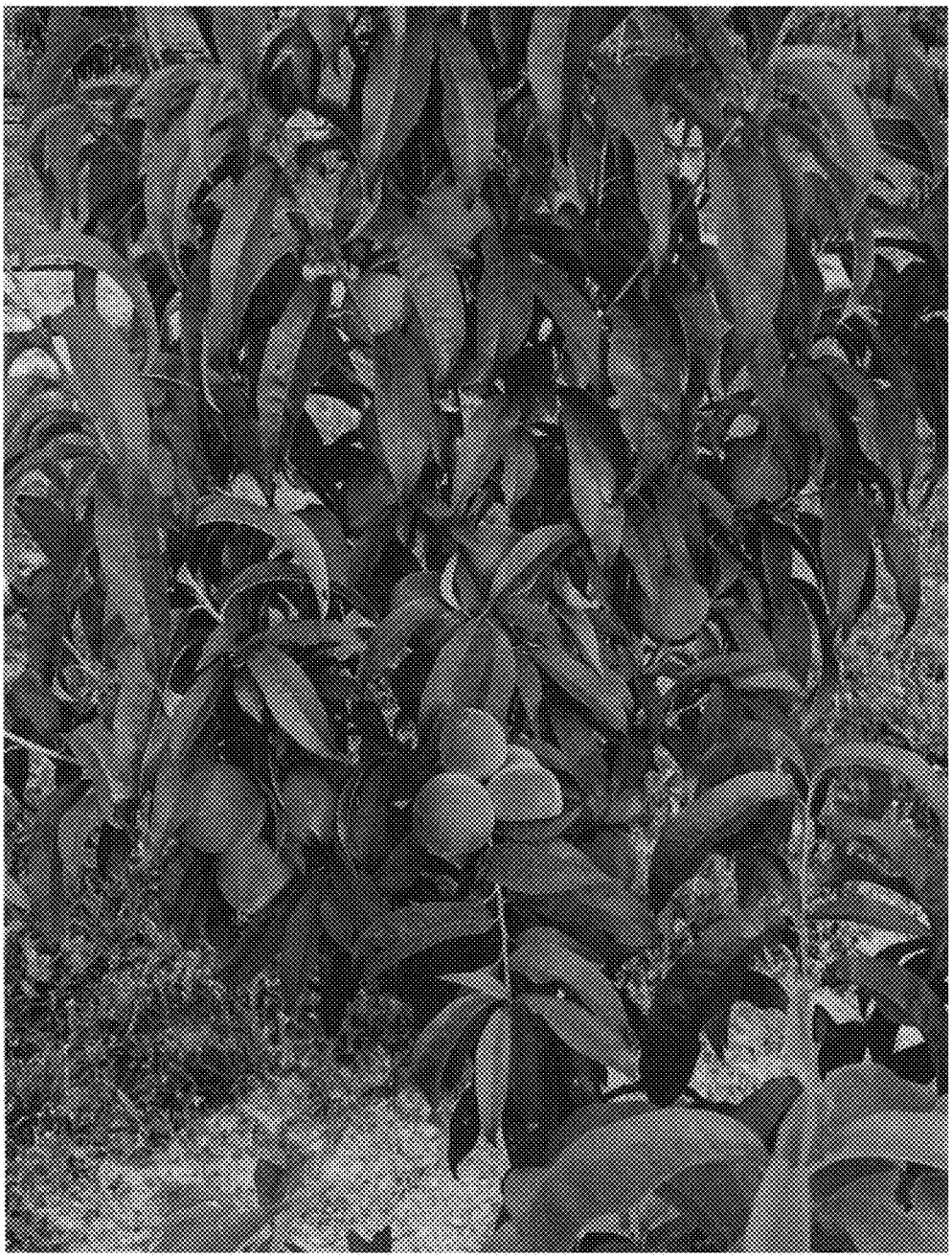
FIG. 3 shows a fruiting tree of the new peach cultivar 'UFRuby' grown in a ground bed in full sun in Gainesville, Fla.

The following detailed description sets forth the distinctive characteristics of the new peach cultivar 'UFRuby'. The present botanical description is that of the new cultivar grown as a five-year-old trees on 'Flordaguard' rootstock under the ecological conditions at Gainesville, Fla. The tree, flowers, and fruit of 'UFRuby' may vary slightly in detail due to variations in soil type, cultural practices, and climatic condition. The potential for commercial production of fresh fruit is high, due to its attractive red skin over a creamy white ground color, medium size fruit of good flavor, and good firmness with even ripening throughout the fruit. In the following description, color references are made to "The Pantone Book of Color," published by H. N. Abrams, Inc., N.Y. (1990), except where general terms of ordinary dictionary significance are used.

BOTANICAL DESCRIPTION

Botanical classification:

*Family*.—Rosaceae.

*Botanical name*.—*Prunus persica*.

*Common name*.—Peach.

*Cultivar*.—'UFRuby'.

Parentage:

*Female or seed parent*.—'Flordabest' (U.S. Plant Pat. No. 20,294).

*Male or pollen parent*.—'AusW' (unpatented).

Plant description:

*Type*.—Tree.

*Ploidy*.—Diploid.

*Plant form*.—Semi-spreading, but easily pruned to a vase shape.

*Plant size*.—Trees are medium in stature when trained to an open vase form.

*Vigor*.—Moderately vigorous, and must be pruned in summer and winter when grown to a vase shape to keep the tree open to get strong fruiting wood in the lower center. Trees typically respond to irrigation and fertilization. Tree growth of 4-6 feet in height and 3-5 feet in width occurs in the first growing season in the field in Gainesville, Fla.

*Density*.—Light to medium in branching habit. Pruning is required to open the tree center to promote sunlight entrance for enhancing fruit color and sugar development.

*Hardiness*.—Hardy with respect to typical north central Florida winters.

*Bearing*.—Very productive annually without alternate bearing observed. Trees are self-fertile and must be fruit thinned to avoid limb breakage and to obtain large fruit size. Trees annually set several times the number of fruit for a desired crop load.

*Chilling requirement*.—Estimated endodormancy chilling requirement is 200 chill units based on the time of bloom and leafing in relation to standard varieties.

*Trunk*.—Size: Medium, trunk attaining a diameter of 8 cm at a height of 30 cm at the end of three years of growth in Gainesville, Fla. Texture: Medium smooth, but changes to medium shaggy as tree ages. Bark color: Older bark is gray (Chinchilla, Pantone 17-1109). Lenticels: Number: Moderate number (6-12 lenticels per 4 $in^2$ of surface area of trunk). Size: Large (6-12 mm in length perpendicular to the trunk). Color: Gray (Sponge, Pantone 16-1118) with the center being yellowish brown (Inca Gold, Pantone 17-1048).

*Branches*.—Size: Strong growth of scaffold branches. Fruiting branches are mostly of large diameter (4-7 mm) and not overly twiggy, resulting in strong fruiting wood. Thus, the tree growth and structure permit easier and faster winter pruning. Texture: Relatively smooth, lenticels of medium size and attaining size found on the trunk and old scaffolds. Roughness increases with age. Color: New wood: Light green (Mellow Green, Pantone 12-0426). Old wood: Brown (Sierra, Pantone 18-1239). Crotch angles: Angles are selected at 45° to near 90° in first year of tree training. Natural angles are within the normal range of standard varieties for a semi-spreading tree and similar to those of other peach cultivars.

Foliage:

*Arrangement*.—Alternate.

*Size*.—Medium; 16-18 cm in length, including the petiole; 41-47 mm in width. Measurements were made on vigorous upright shoots of summer growth.

*Thickness*.—Regular and average for commercial peach varieties. Not noticeably unusual.

*Form*.—Lanceolate.

*Apex*.—Acute.

*Margin*.—Serrulate, slightly undulate.

*Base*.—Cuneate.

*Surface*.—Upper surface: Glabrous. Lower surface: Lower surface has medium-large veins that are pinnately netted.

*Color*.—Lower surface: Green (Sage, Pantone 16-0421). Upper surface: Slightly darker green (Artichoke Green, Pantone 18-0125).

*Glands*.—Number: Usually two, small-size globose glands on lower leaf blade and petiole. Color: Leaf glands on young leaves are light green (Green Moss, Pantone 17-0636). Size: Averages about 1 mm in length and 0.3 mm in width.

*Petiole*.—Size: Averages 1 cm (0.8-1.2 cm) in length and 1.5 mm in diameter. Color: Light green (Tarragon, Pantone 15-0326) on older leaves of summer. Shape: Grooved longitudinally.

*Stipules*.—Number and size: Medium (equal to most commercial peach varieties), usually two per bud and abscising just before leaf becomes full size in summer growth. Color: Color at full size is green (Spinach Green, Pantone 16-0439), but tinged with anthocyanin before abscising.

Inflorescence:

*Flower buds*.—Hardiness: Hardy with respect to north central Florida winters (16° F. minimum temperature observed). Abundance: Very high due to shorter-than-average internode length (average internode length is 20 mm). Most buds set fruit in absence of spring frosts and show little evidence of bud drop. Size: Medium, averages 5 mm in length in mid-winter. Form: Plump, conic, and free. Surface: Pubescent scales. Color: Brown (Stucco, Pantone 16-1412) in late summer.

*Flowers*.—Blossom period: Averages 50% bloom January 17$^{th}$ to February 5$^{th}$ of most years in Gainesville, Fla., but occurring over a 7-10 day period. Time and length of bloom are dependent on ambient temperature. Aroma: Not detectable. Flower density: Abundant, varying one to three per node, but typically two per node. Type: Showy, location and seasonally variable within the range of commercial showy varieties. Average flower diameter: 3.7 cm. Petals: Number: Five. Size: Averages 18 mm in length and 13 mm in width. Average petal width: 13 mm. Texture: Smooth, glabrous. Margins: Undulate and smooth. Color: Light lilac (Light Lilac, Pantone 12-2903) at flower opening, and within the pink range of standard varieties. Stamens and pistils: Sizes, shapes, and colors are within the range of standard commercial varieties. Sepals: Number: Five. Size: Averages 6 mm in length and 6 mm in width at the point of attachment to the calyx cup; rounded at the distal end. Texture: Pubescent. Color, interior: Green (Spinach Green, Pantone 16-0439). Color, exterior: Reddish brown (Brown Stone, Pantone 19-1322). Margins. Smooth pubescent margin. Pistils: Number: Typically one per flower. Form: Straight (without curls or curves) just prior to flower opening. Size: Averages 15 mm in length (from tip of stigma to base of ovary). Color: Light yellow (Canary Yellow, Pantone 12-0633). Pedicel: Size: 1-2 mm in length. Peduncle: Size: Averages 4 mm in length and 3 mm in width. Color: Green (Cedar, Pantone 16-0526). Calyx cup: Size, form: Medium large, in the size range of commercial peach varieties. Calyx cup is noticeably tough to cut in emasculations. Size: 5 mm in diameter at the top, at the time of flower opening. Color, exterior: Red (Barn Red, Pantone 18-1531). Color, interior: Greenish yellow (Golden Rod, Pantone 14-0951). Stamen: Anthers, number: Varies from 33-41. Anthers, color: Deep yellow (Coral Rose, Pantone 16-1349) at flower opening. Filament, length: 10-14 mm. Filament, color: White (Pastel Parchment, Pantone 11-0603) at flower opening. Pollen: Presence: Abundant. Color: Yellow (Snapdragon, Pantone 13-0840). Fertility: Fully self-fertile, and no cross-pollination is required. Fruit set is abundant.

Fruit:

*Maturity when described*.—Tree ripe, Apr. 15, 2021, in Gainesville, Fla.

*Date of picking*.—First picking on Apr. 15, 2021, in Gainesville, Florida; last picking on Apr. 21, 2021, in Gainesville, Fla.

*Size*.—Uniform, medium (medium size for early season maturity at 110-130 g). Size varies with fruit number per tree, soil type, climatic conditions, and cultural practices. Average equatorial diameter: 2.25 in (60 mm). Average polar length (stem to distal end): 2.25 in (60 mm).

*Longitudinal section form*.—Nearly round.

*Transverse section form, through diameter*.—Round.

*Suture*.—Shallow and inconspicuous except for a crease on the stem end of the fruit.

*Ventral surface*.—Usually rounded.

*Base*.—Slightly cordate.

*Apex*.—Usually rounded to slightly obtuse.

*Crater at stem attachment*.—Form: Flaring circular with slight suture crease at the stem end. Size: 9-10 mm in depth, 20 mm in breadth at the top, 5 mm at pedicel attachment.

*Skin*.—Thickness: Medium in comparison to commercial peach varieties. Texture: Medium in comparison to standard peach varieties. Tenacity: Tenacious to flesh. Color: Red (Raspberry Wine, Pantone 18-1741) over 60% to 70% of the skin. Ground color is cream (Dawn, Pantone 12-0811). Fruit exposed to sunlight have a higher degree of enhanced red skin. Tendency to crack: None observed. Taste: No astringency observed. Epidermis: Pubescent.

*Flesh*.—Ripening: Even ripening within each fruit. Texture: Firm, but juicy and non-melting when fully ripe. Fibers: Very fine, small, tender, and abundant. Aroma: Moderate and in the middle range of commercial peach varieties. Eating quality: Good, moderately sweet, slightly acid. Soluble solids average 10-13 brix at 3.2-2.4 kg penetrometer firmness with a standard 5/16 inch tip. Juice: Abundant. Color: White (Bone White, Pantone 12-0105), with some red in the flesh, but none at the pit. Browning by oxidation: Moderate on cut fruit when tree ripe and beginning to soften. Amygdalin: Undetected. Texture: Smooth.

*Stone*.—Type: Clingstone. Size: Medium-small. Averages 30 mm in length, 21 mm in width, 18 mm in thickness, and 6 mm in wall thickness. Color: Light brown (Buckskin, Pantone 16-1342) when flesh is freshly cut. Form: Slightly oblong. Base: Straight. Apex: Rounded. Sides: Near equal. Surface: Irregularly shallowly furrowed. Ridges: Shallow and rounded. Tendency to split: None observed. Seed: Amygdalin: Abundant (kernel is bitter). Viability: Viable if stratified upon removal from fruit at harvest and cultured on a germination medium. Color: Kernel is brown (Gold Earth, Pantone 15-1234) when first removed from ripe fruit. Size: 16 mm in length, 10 mm in width, 5 mm thick. Shape: Acute tip with obtuse base and overall ovate shape.

*Use*.—Fresh; dessert.

Resistance to diseases and pests: High resistance to bacterial spot incited by *Xanthomonas campestris* pv. *pruni* (Pers.) Diet. Resistance to other fruit and tree diseases are within the range for commercial peach cultivars in Florida. No unusual resistance or susceptibility to insects and diseases noted.

Keeping quality: Excellent after ten days at 2° C. and with minimal bruises or scarring appearing on skin.

Shipping quality: Degree of firmness at harvest and firmness retained in refrigeration for ten days at 2° C., with no internal breakdown of flesh or appreciable loss of eating quality, which indicates fruit should be highly acceptable for shipping.

I claim:

1. A new and distinct tree named 'UFRuby' as illustrated and described herein.

* * * * *